United States Patent
Loos

[11] Patent Number: 6,167,304
[45] Date of Patent: Dec. 26, 2000

[54] PULSE VARIABILITY IN ELECTRIC FIELD MANIPULATION OF NERVOUS SYSTEMS

[76] Inventor: Hendricus G. Loos, 3019 Cresta Way, Laguna Beach, Calif. 92651

[21] Appl. No.: 09/336,369

[22] Filed: Jun. 17, 1999

Related U.S. Application Data

[63] Continuation-in-part of application No. 09/118,505, Jul. 17, 1998, Pat. No. 6,081,744, which is a continuation-in-part of application No. 08/788,582, Jan. 24, 1997, Pat. No. 5,782,874, which is a continuation-in-part of application No. 08/447,394, May 23, 1995, abandoned, which is a continuation of application No. 08/068,748, May 28, 1993, abandoned.

[51] Int. Cl.$^7$ ..................................................... A61N 1/40
[52] U.S. Cl. ................................................................ 607/2
[58] Field of Search .................................... 607/2, 39, 46

[56] References Cited

U.S. PATENT DOCUMENTS

| | | | |
|---|---|---|---|
| 1,973,911 | 9/1934 | Ruben | 607/152 |
| 3,678,337 | 7/1972 | Graetzel | 128/419 N |
| 3,840,020 | 10/1974 | Smith | 128/419 N |
| 3,886,932 | 6/1975 | Suessmilch | 128/908 |
| 3,941,136 | 3/1976 | Bucalo | 607/39 |
| 4,084,595 | 4/1978 | Miller | 128/422 |
| 4,197,851 | 4/1980 | Fellus | 128/422 |
| 4,297,980 | 11/1981 | Suzuki | 128/419 N |
| 4,611,599 | 9/1986 | Bentall et al. | 178/422 |
| 4,856,526 | 8/1989 | Liss et al. | 128/422 |
| 5,169,380 | 12/1992 | Brennan | 600/26 |

FOREIGN PATENT DOCUMENTS

| | | | |
|---|---|---|---|
| 0285415 | 12/1965 | Australia | 607/2 |
| 3327126 | 4/1984 | Germany | 607/2 |
| 2164563 | 3/1986 | United Kingdom | 607/2 |

OTHER PUBLICATIONS

N. Wiener, Nonlinear Problems in Random Theory, 1958, p. 71,72 M. Hutchison, MegaBrain, 1991, p. 233,245.

*Primary Examiner*—William E. Kamm

[57] ABSTRACT

Apparatus and method for manipulating the nervous system of a subject by applying to the skin a pulsing external electric field which, although too weak to cause classical nerve stimulation, modulates the normal spontaneous spiking patterns of certain kinds of afferent nerves. For certain pulse frequencies the electric field stimulation can excite in the nervous system resonances with observable physiological consequences. Pulse variability is introduced for the purpose of thwarting habituation of the nervous system to the repetitive stimulation, or to alleviate the need for precise tuning to a resonance frequency, or to control pathological oscillatory neural activities such as tremors or seizures. Pulse generators with stochastic and deterministic pulse variability are disclosed, and the output of an effective generator of the latter type is characterized.

11 Claims, 5 Drawing Sheets

PULSE VARIABILITY IN ELECTRIC FIELD MANIPULATION OF NERVOUS SYSTEMS

This application is a Continuation-in-Part of Ser. No. 09/118,505, Jul. 17, 1998, U.S. Pat. No. 6,081,744 which is a Continuation-in-Part of Ser. No. 08/788,582, Jan. 24, 1997, U.S. Pat. No. 5,782,874, which is a Continuation-in-Part of Ser. No. 08/447,394, May 23, 1995, abandoned, which is a Continuation of Ser. No. 08/068,748, May 28, 1993, abandoned.

BACKGROUND OF THE INVENTION

The invention relates to the stimulation of the nervous system of humans by an electric field applied externally to the body. A neurological effect of external electric fields has been mentioned by Norbert Wiener [1], in discussing the bunching of brain waves through nonlinear interactions. The electric field was arranged to provide "a direct electrical driving of the brain" [1]. Wiener describes the field as set up by a 10 Hz alternating voltage of 400 V applied in a room between ceiling and ground.

Brennan [2] describes an apparatus for alleviating disruptions in circadian rythms of a mammal, in which an alternating electric field is applied across the head of the subject. The voltage applied to the electrodes is specified as at least 100 V, and the peak-to-peak value of the electric field as at least 590 V/m in free air before deploying the electrodes across the head of the subject. The frequency of the alternating electric field is in the range from 5 to 40 Hz. Brennan states that the method is aimed at subjecting at least part of the subject's brain to an alternating electric field. It should be noted that electric polarization of the head causes the field strength in the narrow space between electrode and skin to be about a factor h/2d larger than the free-air field strength, h being the distance between the electrodes and d the spacing between electrode and skin. For h=17 cm and d=5 mm the factor comes to 17, so that with the specified free-air field of at least 590 V/m the field in the gap between electrode and skin is at least 10 KV/m peak to peak.

A device involving a field electrode as well as a contact electrode is the "Graham Potentializer" mentioned in Ref. [3]. This relaxation device uses motion, light and sound as well as an alternating electric field applied predominantly to the head. The contact electrode is a metal bar in Ohmic contact with the bare feet of the subject; the field electrode is a hemispherical metal headpiece placed several inches from the subject's head. According to the brief description in [3], a signal less than 2 V at a frequency of 125 Hz is applied between the field electrode and the contact electrode. In this configuration the contact electrode supplies to the body the current for charging the capacitor formed by the field electrode and the apposing skin area. The resulting electric field stands predominantly in the space between the head piece and the scalp.

In the three external field methods mentioned, viz. Wiener [1], Brennan [2], and Graham [3], the electric field is applied to the head, and the brain is thereby exposed to polarization currents. These currents run through the brain in a broad swath, with a distribution influenced by nonuniformities of tissue conductivity and permittivity. The scale of the current density can be conveniently expressed by the maximum value, over the skin of the head, of its component perpendicular to the local skin. This scale is easily calculated for sinusoidal fields as the product of radian frequency, vacuum permittivity, and maximum amplitude of the external field on the head. Using Brennan's [2] lowest frequency of 5 Hz, his miniumum required free-air field strength of 590 V/m, and the factor 17 estimated above to account for the polarization of the head by the applied field, the scale of the polarization current density in the brain comes to about 280 pA/cm$^2$. Although such a current density would generally be considered very small in electrophysiology, a repetitive application at certain critical frequencies and along certain paths in the brain may perhaps cause kindling in individuals predisposed to epilepsy, and it is therefore deemed too large for use by the general public. Conservatively, we consider polarization current densities in the brain with a scale in excess of 70 fA/cm$^2$ to be substantial.

It is the object of the present invention to obtain a method and apparatus for manipulating the nervous system by externally applied electric fields without causing substantial polarization current densities in the brain.

The use of electric fields raises concerns about possible health effects. Such concerns have been widely discussed in the media in regard to electric power lines and electric apparatus [4]. Answering the pertinent questions by objective research will take time, but meanwhile governments have been setting guidelines for safe limits on field strengths. At present, the strictest limits of this sort are the Swedish MPRII guidelines. Magnetic fields are of no concern here, because the currents involved are so small. However, the electric field strengthy must be considered, since even at low voltages strong electric fields can result from electrodes placed close to the skin. For fields of extremely low frequency the MPRII guidelines limit the field strength to 25 V/m in the frequency range from 5 Hz to 2 KHz. In the Brennan patent [2] the minimum field strength of 590 V/m violates these guidelines by a factor 23; when the polarization effects are accounted for, the factor is about 400.

It is a further object of the present invention to manipulate the nervous system by external electric fields that are in compliance with the MPRII guidelines.

Brennan [2] stipulates voltages of at least 100 V, and as high as 600 V for his preferred embodiment. Generation of such voltages requires a voltage multiplier stage, if practical battery operation is desired. This increases the current drain and the size of the generator. The large voltages also raise safety concerns.

It is yet a further object of the present invention to manipulate the nervous system by external electric fields, using low voltages that are generated by small and safe battery-powered devices with low current consumption.

The nervous system generally habituates to repetitive stimuli. It is still a further object of the present invention to manipulate the nervous system by externally applied electric fields in such a manner as to thwart habituation.

SUMMARY

Experiments have shown that weak electric fields of frequency near ½ Hz applied externally to the skin of a subject can cause relaxation, doziness, ptosis of the eyelids, or sexual excitement, depending on the skin area of application and the precise frequency used. In these experiments the electric field was applied predominantly to selected skin areas away from the head, thereby avoiding substantial polarization current densities in the brain. Apparently, the external electric field influences somatosensory or visceral afferent nerves, which report the effect to the brain. Although the mechanism whereby the field acts on the afferents is unknown, the effect must take the form of a modulation of the spiking patterns of the nerves, because the electric current densities induced in the tissue are much too small to cause firing of a normally quiescent nerve. If the applied external field is periodic, so will be the modulation of the spiking patterns of affected afferent fibers, and the brain is thus exposed to an evoked periodic signal input. It appears that this signal excites certain neural circuits to resonance, with observable consequences. Since the resonances are excited through somatosensory or visceral afferents, they are called "sensory resonances".

Besides the resonance near ½ Hz that affects the autonomic nervous system, we have also found a resonance near 2.4 Hz which slows certain cortical processes. For both resonances the strength of the external electric field on the skin must lie in a certain range for the physiological effects to occur. This range, which is called the "effective intensity window", depends on the number of afferents modulated by the field. When a large skin area is exposed, the field strengths at the lower window boundary are very small. The effectiveness of weak fields allows the use of small battery-powered electric field generators that can be used conveniently by the general public as an aid to relaxation, sleep, or sexual excitement, and clinically for control and perhaps treatment of tremors and seizures, and disorders of the autonomic nervous system such as panic attacks.

Compliance of the devices with the MPRII guidelines on field limits in the ELF and VLF frequency bands is easily achieved, because reliance on the resonance mechanism allows the use of weak fields.

The field generators shown involve simple low voltage pulse generators based on 555-type timer chips. The field electrodes can be made small enough to fit, together with the generator, in a single small casing.

Habituation of the nervous system to the electric field stimulation can be thwarted to a considerable extent by introducing variability into the field pulses. Simple circuits are shown that provide stochastic and deterministic pulse variability. The output of a circuit with the latter variability has been measured and characterized. In experiments, the small battery-powered device with this circuit has consistently induced in a male subject sexual excitement for up to an hour duration.

DETAILED DESCRIPTION

It has been found in our laboratory that weak pulses of electric field acting externally on the skin can influence the nervous system of a human subject, if the pulse frequency is near ½ Hertz. The external electric field may be generated by applying voltage pulses to field electrodes that have no electric contact with the subject; the electrodes may even be placed at a considerable distance. The observed physiological effects include ptosis of the eyelids, relaxation, drowsiness, the feeling of pressure at a centered spot on the lower edge of the brow, seeing moving patterns of dark purple and greenish yellow with the eyes closed, a tonic smile, a tense feeling in the stomach, sudden loose stool, and sexual excitement, depending on the precise frequency used, and the skin area to which the field is applied.

In these experiments the polarization current densities induced in the biological tissue are much too small to cause classical nerve stimulation, wherein the nerve membrane is depolarized sufficiently for the normally quiescent nerve to fire. Signal pathways to the brain other than afferent nerves have been ruled out by experiments. Apparently, a weak pulsed external electric field can modify the signals emitted by sensory or visceral receptors, which are then transmitted to the brain along afferent nerves. Since classical nerve stimulation cannot occur, the signal modification must have the form of a modulation of spontaneously occurring spiking patterns. The simplest such modulation is frequency modulation (fm), but more subtle modulation modes [5] may be involved. In our experiments the modulation is very shallow, but the fm signal can evidently excite a resonance in certain neural circuits, and thereby have observable consequences. Since the applied fields are much too weak to cause firing of normally quiescent nerves, only those sensory and visceral receptors that normally feature spontaneous spiking can be respond to the weak fields.

The resonances that are excited through somatosensory or visceral afferent nerves are called sensory resonances. The sensory resonance near ½ Hz involves the autonomic nervous system and is sometimes referred to as the ½ Hz autonomic resonance.

Exploitation of sensory resonances and reliance on modulation of spontaneous spiking patterns rather than on classical nerve stimulation makes it possible to manipulate the nervous system with very small external electric fields that are induced by low voltages applied to field electrodes. Moreover, using the natural pathways of afferent nerves for putting manipulatory signals into the brain makes it possible to obtain desirable physiological effects while applying the field to skin areas away from the head. The invention thereby meets the stated objects of providing manipulation of the nervous system without causing substantial polarization current densities in the brain, compliance with MPRII field limits, and use of low-voltage battery-powered generators with small current consumption.

The invention provides a method and apparatus for maniplating the nervous system of human subjects. Such manipulation comprises relaxation and the induction of sleep or arousal, as well as control and perhaps treatment of tremors, seizures, and disorders resulting from a malfunction of the autonomic nervous system, such as panic attacks.

In the early experiments the excitation of the sensory resonance was done through the modulation of cutaneous nerves by a weak applied electric field. Later on, similar physiological effects have been obtained by applying a much stronger field to the skin overlying the vagus nerve or the sciatic nerve.

A new sensory resonance has been found near 2.4 Hz. The resonance is characterized by a pronounced increase in the time needed for silently counting backward from 100 to 60, with the eyes closed. Prolonged exposure to the excitation was found to have a sleep-inducing and dizzying effect. Discovery of other sensory resonances may be expected.

The equipment suitable for the generation of the weak electric fields used for the modulation of afferent nerves consists of field electrodes and a generator of voltage pulses. The field electrodes can be conductive foils, wires or meshes that optionally may be covered on one or both sides with an insulating layer. The field electrodes are to be electrically connected to the generator, but insulated from the subject. The voltage generator is to produce a low pulsing voltage. Harmonic content needs to be considered for compliance with MPRII guidelines, if the field applied to the skin is strong. An automatic shutoff may be provided, such as to limit the duration of the field administration.

It has been found that half an hour of field application is usually sufficient to induce sleep, if the field is tuned correctly for the individual to a frequency near ½ Hz. Shorter application times are typically sufficient for inducing relaxation.

The mentioned physiological effects are observed only when the strength of the electric field on the skin lies in a certain range, called the effective intensity window. We also have observed a bulk effect, in that weaker fields suffice when they are applied to a larger skin area. The effective intensity window and the bulk effect are discussed in detail in earlier patents [6,7].

Figure 1:
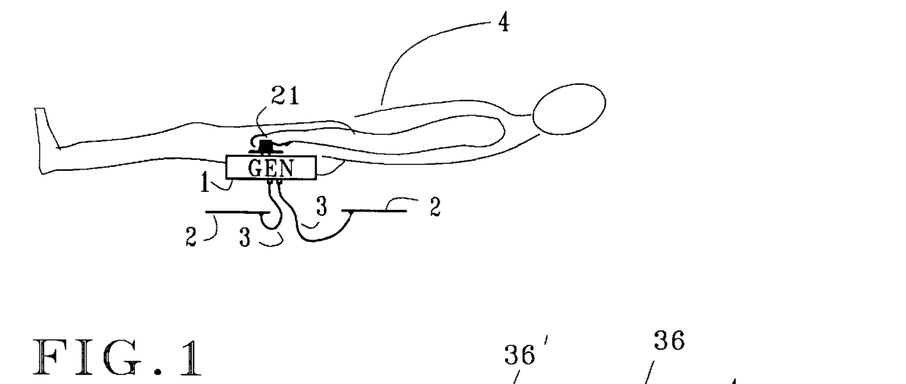
FIG. 1 shows the application of an electric field by field electrodes placed externally to a subject.

An embodiment of the invention is shown in FIG. 1, where the voltage pulse generator 1, labelled as "GEN", is connected to the field electrodes 2 by wires 3; the field electrodes 2 are positioned away from and on one side of the subject 4. The voltage generator may be tuned manually with the tuning control 21.

Figure 2:
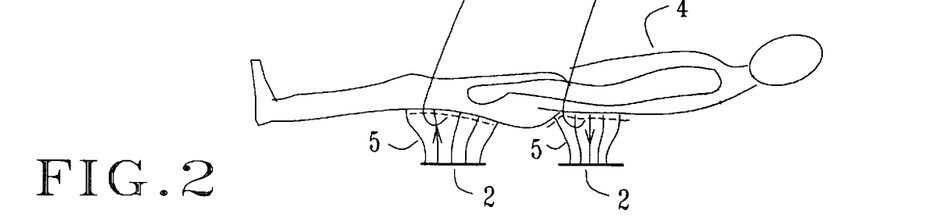
FIG. 2 illustrates the electric field generated between the field electrodes and the subject's body.

The electric field 5 induced between the field electrodes 2 and the subject 4 is illustrated in FIG. 2. The electric field is applied predominantly to certain areas of the skin of the subject, such as areas 36 and 36'. The skin area of predominant field application is defined as the set of points on the skin at which the absolute value of the resultant field strength is at least twice the average over the skin. The resultant field includes the electric field produced by polarization charges that arise on the skin in response to the externally generated field.

Figure 3:
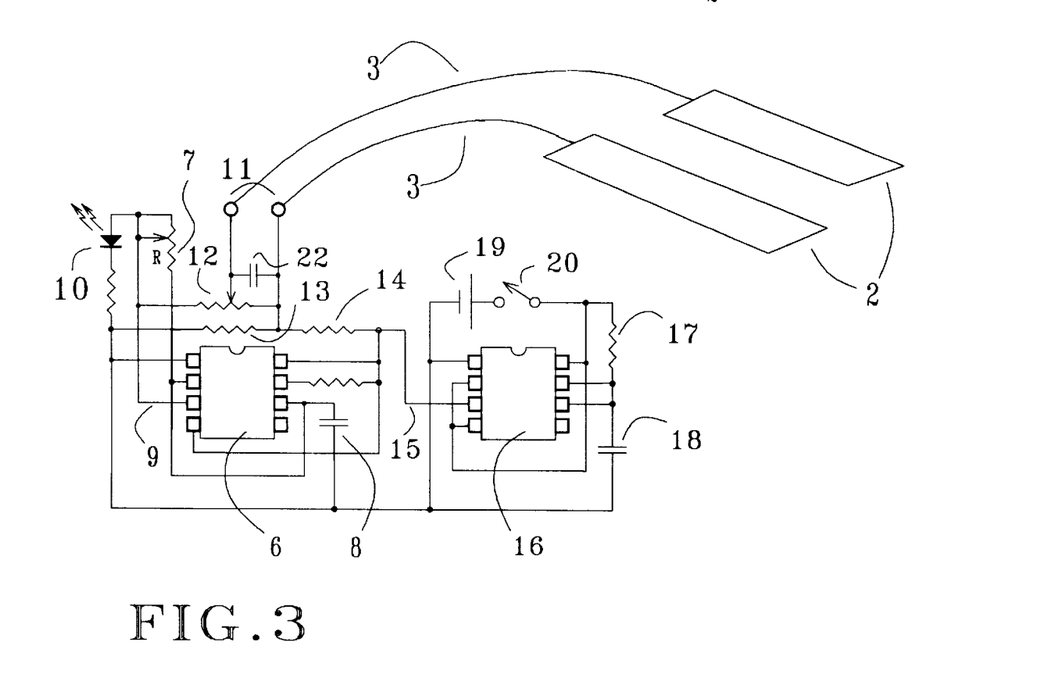
FIG. 3 shows an embodiment which generates a rounded square-wave electric field, and includes an automatic shut-off.

A suitable pulse generator, built around two RC timers, is shown in FIG. 3. Timer 6 (Intersil ICM7555) is hooked up for astable operation; it produces a square-wave voltage with a frequency determined by potentiometer 7 and capacitor 8. The square-wave voltage at output 9 drives the LED 10 and appears at one of the output terminals 11, after voltage division by potentiometer 12. The other output terminal is connected to an intermediate voltage determined by the resistors 13 and 14. As a result, the voltage between the output terminals 11 alternates between positive and negative values. Automatic shutoff of the voltage that powers the timer at point 15 is provided by a second timer 16 (Intersil ICM7555), hooked up for monostable operation. The shutoff occurs after a time interval determined by resistor 17 and capacitor 18. Timer 16 is powered by a battery 19, controlled by the switch 20. The output terminals 11 are connected to the field electrodes 2 by conductors 3. The resistors 13 and 14 not only serve as a voltage divider that gives the intermediate voltage needed to produce an alternating square wave, but provide current limitation as well. The currents induced in the subject may be further decreased by using an output capacitor 22.

The skin area of predominant field application may be selected such as to maximize the desired physiological effect. For use of a sleeping aid, a good choice is shown in FIG. 2, where the field is predominantly applied to a skin area 36 on the hips, buttocks, and lower back and another skin area 36' on the back side of the thighs and knees. For sexual excitement the field is best applied to at least part of the skin covering the scrotum, perineum, anus, and sacral spine.

It is often important to thwart habituation of the nervous system to the repetitive stimulation provided by the electric field pulses. In the present invention this is done by introducing variability in the pulses. Such variability may comprise amplitude modulation, frequency modulation, or phase modulation of the electric field pulses. Since signals are propagated along nerve axons as action potentials of essentially fixed amplitude and pulse shape, the important signal feature is timing, so that frequency or phase modulation is expected to be especially effective in thwarting habituation.

Pulse variability may be used for purposes other than thwarting habituation, for instance alleviating the need for precise tuning to a resonance frequency. This may be important when sensory resonance frequencies are not be known precisely, because of variation among individuals, or in order to cope with the frequency drift that results from chemical modulation [6]. An electric field with properly chosen pulse variability can then be more effective than a fixed frequency field that is out of tune.

One may also control tremors and seizures, by interfering with the pathological oscillatory activity of neural circuits that occurs in these disorders. Electric fields with a pulse variability that results in a narrow spectrum of frequencies around the frequency of the pathological oscillatory activity may evoke nerve signals that cause phase shifts which diminish or quench the oscillatory activity.

Figures 4, 17:
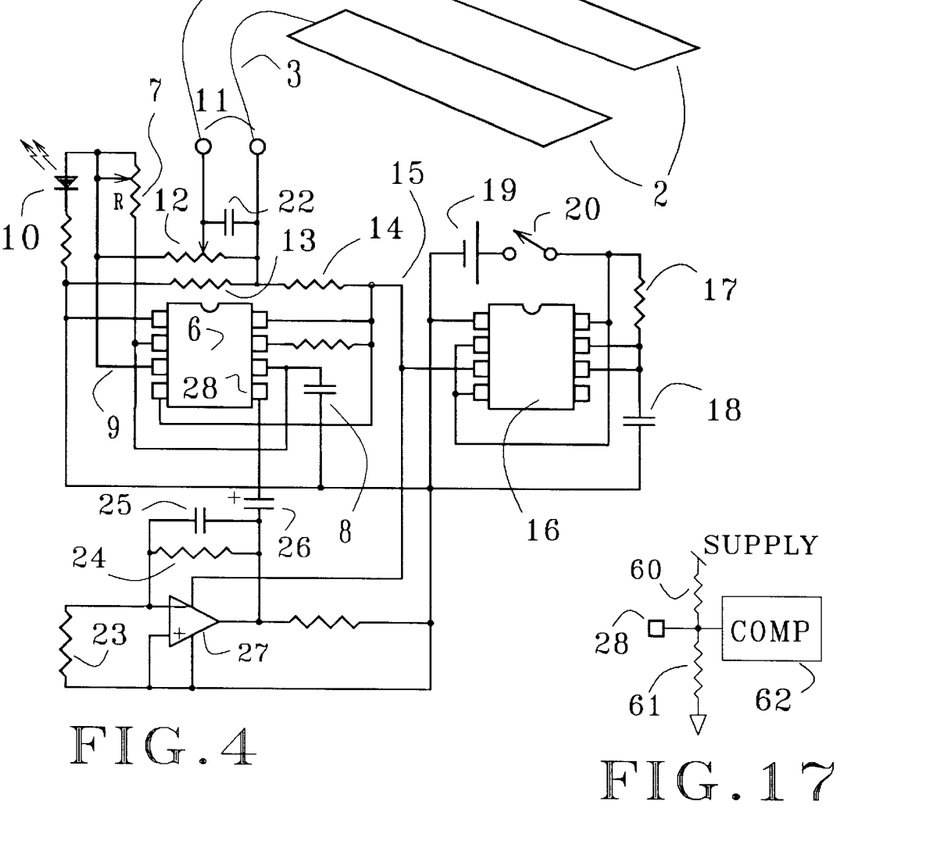
FIG. 4 shows an electric field generator with stochastic pulse variability.
FIG. 17 shows schematically the control circuit for influencing the pulse intervals of an RC timer.

A convenient means for introducing pulse variability is to generate the pulses with an RC timer that includes a control circuit for influencing the pulse intervals, shown schematically in FIG. 17. The circuit includes a comparator 62 which compares the timing capacitor voltage with the voltage on the control voltage port 28 of the timer chip. If this port is left unconnected, its voltage is internally set to ⅔ of the supply voltage, by a divider consisting of the resistors 60 and 61, where $R_{61}=2R_{60}$. When the capacitor voltage in the timer surpasses the control voltage, the comparator trips and causes the capacitor to discharge abruptly. Pulse variability can thus be introduced by externally injecting a fluctuating current into the control voltage port of the timer chip. A simple pulse generator with stochastic pulse variability based on this method is shown in FIG. 4, where the control voltage port 28 of timer 6 is connected to a stochastic voltage source. This source is derived from the noise voltage of a resistor 23 that is amplified by the operational amplifier 27, which has a feedback circuit consisting of resistor 24 and capacitor 25. The amplifier output is connected to the control voltage port 28 of the timer 6 via the dc-blocking capacitor 26. The control voltage is thereby perturbed in a stochastic manner away from its normal value of ⅔ of the supply voltage.

The main frequency of the pulse train, to be defined later, is determined by the setting of the potentiometer 7, which therefore serves as a tuning control. If desired, the voltage pulses may be rounded by an RC circuit or an integrator stage.

Figure 5:
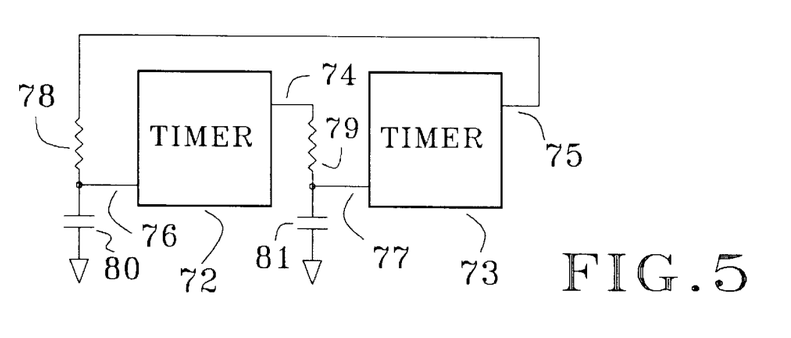
FIG. 5 shows schematically how to obtain pulse variability with two cross-coupled RC timers.

Deterministic variability of square-wave pulses may be obtained by cross coupling two RC timers. FIG. 5 shows such a hookup where timers 72 and 73, each labeled "TIMER", serve as voltage pulse generators, and have their output pins 74 and 75 connected crosswise to each other's control voltage pins 76 and 77, via resistors 78 and 79. For brevity, these resistors may be seen as part of the voltage pulse generators so that they do not need to be mentioned explicitly. The control voltage pins 76 and 77 have capacitors 80 and 81 to ground. If the timers are hooked up for astable operation with slightly different frequencies, and the coupling resistors and capacitors are chosen appropriately, then the output of either timer is a square wave with deterministic variability. Example circuit parameters are: $R_{78}=440$ K$\Omega$, $R_{79}=700$ K$\Omega$, $C_{80}=4.7$ $\mu$F, $C_{81}=4.7$ $\mu$F, with $(RC)_{72}=0.83$ second and $(RC)_{73}=1.1$ second. Tests on a subject who has a hand tremor of non-Parkinson origin have shown good control of the tremor by an external electric field induced by the voltage pulses produced by the generator of FIG. 5. In these tests the subject was seated in an easy chair, with the field electrodes placed vertically on two opposite sides of the seat cushion.

Figure 6:
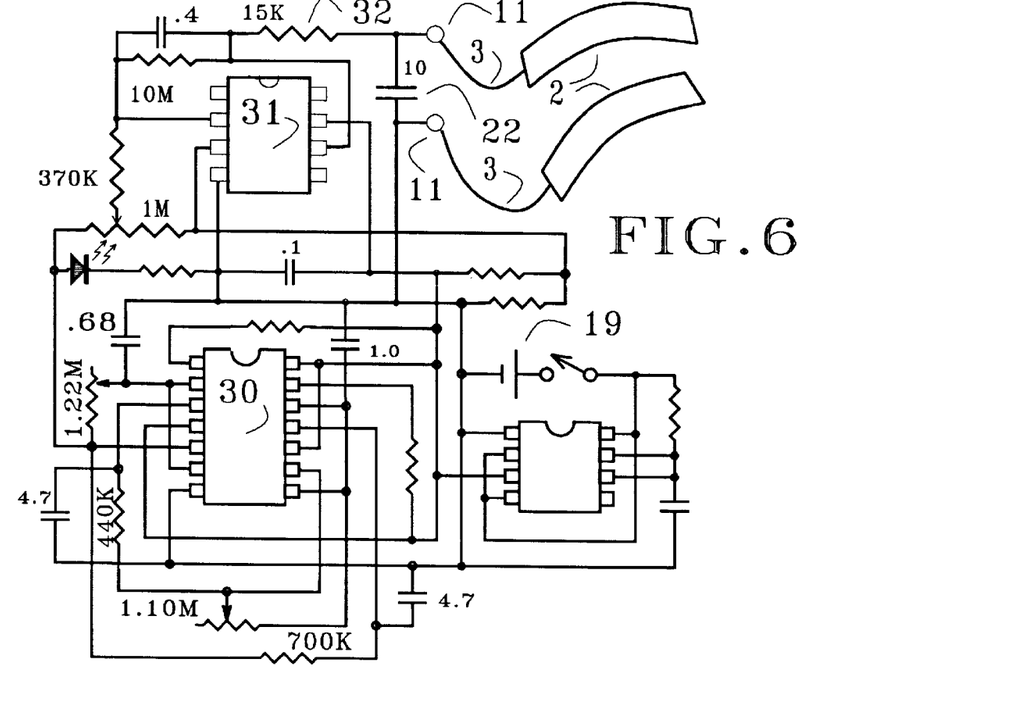
FIG. 6 shows the preferred embodiment with an electric field generator that produces rounded pulses with deterministic pulse variability, employing the method of cross-coupled timers of FIG. 5.
Figure 7:
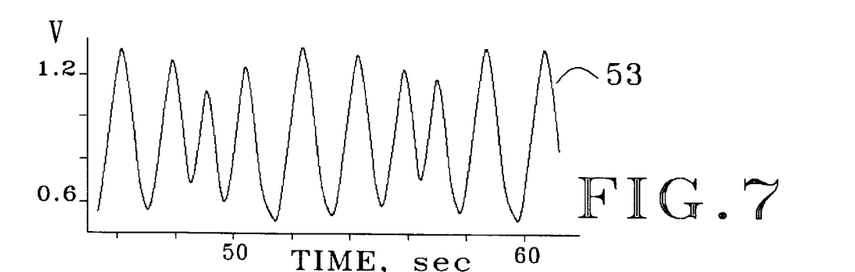
FIG. 7 is a sample of the measured output voltage of the generator of FIG. 6, showing variability of the voltage pulses.

Since the polarization currents that accompany steep pulses may have an irritating effect, rounded pulses are desired if charge modulation [6,7] is relied on for the stimulation of cutaneous sensory receptors. The preferred embodiment shown in FIG. 6 involves a circuit wherein such rounding is achieved by an integrating output stage, and the method of FIG. 5 is used to introduce pulse variability. In FIG. 6 the output signal from the cross-coupled double timer 30 is processed by the integrator 31 and is further rounded by an output circuit consisting of the resistor 32 and capacitor 22. A micropower operational amplifier (MAX480) is used as the integrator 31, so that the generator can be powered by a three-volt battery 19 consisting of two AAA cells. Field electrodes 2 are connected to the output terminals 11 by wires 3. A sample voltage 53 measured at the terminals is shown in FIG. 7; the pulse variability is clearly seen. The device of FIG. 6 has been tested oil a male subject, using two field electrodes consisting of aluminum foil strips of 225 by 41 mm insulated on both sides by mylar film. With one insulated electrode wrapped around the scrotum and the other placed on the sacral spine, anus, and perineum, the device was consistently effective in causing sexual excitement lasting as long as an hour.

Figure 8:
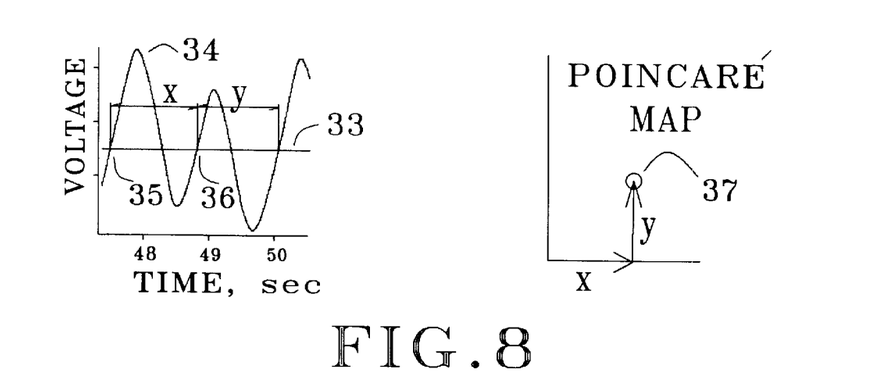
FIG. 8 illustrates the definition of a pulse through rising mean crossings, the pulse interval x, and the next pulse interval y, and shows thow to construct the Poincare map of pulse points (x,y).

In discussing pulse trains such as the measured voltage signal 53 shown in FIG. 7, pulse variability needs to be characterized, and this requires stipulating what is meant by a pulse. Without knowing the relevance to the nervous system, we choose here a definition that is most convenient for data analysis. As illustrated in FIG. 8, the rising signal crossings with the long-time mean voltage 33 are used to partition the signal into pulses, so that pulse 34 is defined as starting at the rising mean crossing 35, and ending at the next rising mean crossing 36. The duration of a pulse is called the pulse interval x. Its average <x> over the pulse train or an appropriate portion thereof is used to define a frequency $f_m=1/<x>$, called the main frequency of the pulse train, or briefly the main frequency of the pulses. The definition circumvents the need for the notion "frequency of an individual pulse", which in general would be an oxymoron. An important tool for the discussion of pulse variability is the Poincare map, in which each pulse in a train is represented by a so-called pulse point (x,y) in a Cartesian coordinate system, x being the pulse interval and y the next pulse interval. The assignements are illustrated in FIG. 8, where x and y for pulse 34 are shown on the left, and the representative pulse point 37 in the Poincare map is shown to the right.

Figure 9:
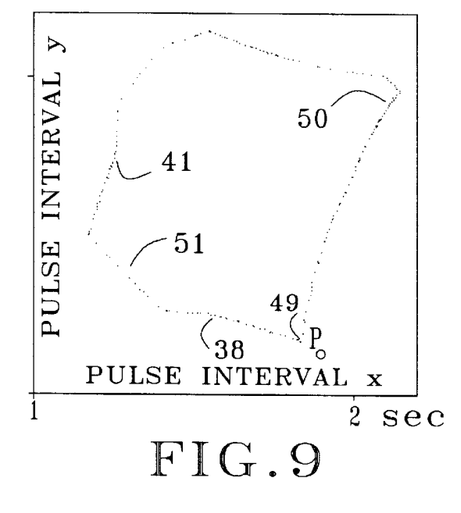
FIG. 9 shows the Poincare map and the attractor for the output voltage of the generator of FIG. 6.
Figure 10:
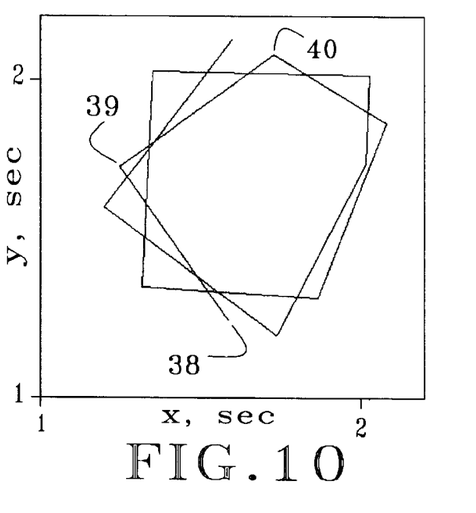
FIG. 10 shows the first eleven transitions in the Poincare map of FIG. 9.

The Poincare map for a train of about two hundred pulses that were measured at the output 11 of the generator of FIG. 6 is shown in FIG. 9. For these measurements the pulse generator was not powered by a battery, but by a five-volt power supply in order to assure steady device operation. The sequence of pulse points in the Poincare map may be indicated by lines that lead from one pulse point to the next. In FIG. 10, the starting pulse is represented by pulse point 38, the next pulse by pulse point 39, the next one by point 40 and so on, in what appears to be a clockwise winding motion. The pulse points in the Poincare map of FIG. 9 appear to lie on a closed curve, shown as 41 in FIG. 11. This curve is called the attractor [8], so named because successive pulse points are drawn to it in time. The attractor was constructed from the set of about two hundred pulse points of FIG. 9 by connecting nearest neighbors, starting with the first pulse point 38. The approach to the attractor does not show up in FIG. 9, because on purpose the voltage measurements were begun after the generator had been in operation for several minutes, when the effect of initial conditions could no longer be felt; the resulting pulse train is called mature.

If the pulse variability were random, the pulse points in the Poincare map of a mature pulse train would be spread over an area of the plane; however, for the pulse train produced by the generator of FIG. 6 the attractor appears to be a closed curve. This shows that the pulse variability has a certain amount of order, which of course reflects the generator structure. Careful inspection of the pulse points in FIG. 9 or FIG. 11 reveals slight irregularities in the attractor 41. This is attributed to generator noise and rounding errors in the analog-to-digital converter, and one may expect that the irregularities disappear in the ideal case where these effects are absent. The following discussion pertains to this case.

Figure 11:
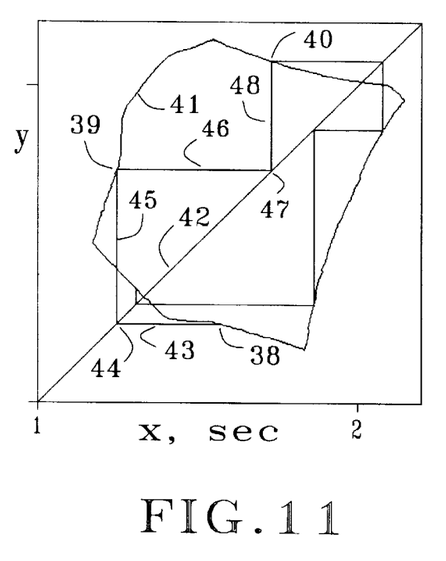
FIG. 11 shows how the pulse points for a mature pulse train can be found from the attractor.

An attractor in the form of a closed curve has the important property that, once an initial pulse point is known, the subsequent pulse points in the Poincare map are determined by the attractor. The construction of the pulse points from the attractor is illustrated in FIG. 11, which shows the attractor 41 and the diagonal 42 on which y=x. Starting at the initial pulse point 38, the next pulse point 39 is found by drawing horizontal and vertical lines as shown in the drawing. The geometric entity comprised of the horizontal 43 from pulse point 38 to point 44, and the vertical 45 from point 44 to pulse point 39 is called a hook. Point 44 is constraint to lie on the diagonal 42. The next pulse point 40 is constructed similarly with the hook consisting of the horizontal 46 and the vertical 48. The role of the diagonal in the construction follows from the fact that in a train of pulses labelled by the index i=1, 2, 3, . . . , one has $x_{i+1}=y_i$, in view of the definition of x as a pulse interval and y as the next pulse interval. Ambiguities in the construction are avoided by the following rules: 1) A hook that lies entirely inside the attractor must not cross the diagonal. 2) A hook that does not lie entirely inside the attractor has three points in common with the attractor. The second rule does not apply when the hook is tangent to the attractor, but then there is no ambiguity either.

Going, in a mature pulse train, from a pulse to the next pulse is represented in the Poincare map as a point transformation T. In FIG. 10, T transforms point 38 of the attractor into point 39 of the attractor. But T also transforms point 39 of the attractor into point 40 of the attractor, etc, so that T is a transformation of at least part of the attractor 41 onto itself. Performing the transformation twice in succession is another such transformation, denoted by $T^2$. Therefore, in FIG. 9 all pulse points are the images of a single point 38 under the first two hundred or so transformations $T^0=I$, T, $T^2$, $T^3$, . . . , where I is the identity transformation. When the above sequence is extended indefinitely, the transformations together with the inverses $T^{-1}, T^{-2}, \ldots$, form a discrete group G of transformations of at least part of the attractor onto itself. G will be called the pulse group. If there is a positive integer m such that $T^m=I$, then the pulse group G is finite; if m is the smallest such integer, the sequence of pulse intervals repeats itself after m pulses, and the pulse intervals are said to be periodic of order m. For example, the train 88 of FIG. 15 has pulse intervals that are periodic of order three. The pulse points shown in FIG. 9 are images of the original pulse point 38 under successive powers of the transformation T, so that they may be called iterated images of the original pulse point. For the measured pulses all iterated images are found to be different, although some lie close together. The closeness is expected, since an infinite set of points on a finite curve must have at least one limit point, by a well-known theorem of analysis.

Introducing the pathlength s along the attractor, measured in clockwise direction from a starting point 49 labeled in FIG. 9 as $P_0$, the transformation T may be represented by the function s'=f(s), where s' is the pathlength of the image of the pulse point with pathlength s. The construction and rules discussed suggest that this function is monotone, provided that one adheres to the convention of increasing the pathlength in every transformation step, even when the starting point $P_0$ is passed. In FIG. 9 one notices along the attractor regions of different pulse point density ρ, such as the high-density region 50 and the low-density region 51. For infinite pulse groups, the differences in densities are due to the nonuniformity of the Jacobian ds'/ds of the transformation function f(.). The Jacobian can be easily calculated from the slopes of the attractor at points s and s'=f(s). It appears that the Jacobians of the transformations T, $T^2$, $T^3$, . . . oscillate rather than increase indefinitely. Hence, under the transformation group G, the iterated images of two neighboring pulse points will remain near each other, so that the excessive sensitivity to initial conditions popularly called the "butterfly effect" [9] is absent, and the transformations are not chaotic. Although the density ρ of iterated images of a pulse point varies over the attractor, it is expected that for an infinite pulse group the iterated images of any pulse point come arbitrarily close to every point on the attractor, i.e., the transformations are ergodic [8]. However, the transformations are not expected to be mixing [8]. For a finite pulse group the iterated images form a finite point set. If the pulse train is periodic of order 1, all pulse intervals are the same, and the attractor consists of a single point on the diagonal. In this case, any pulse variability must be due to differences in pulse shape rather than pulse interval.

Figure 12:
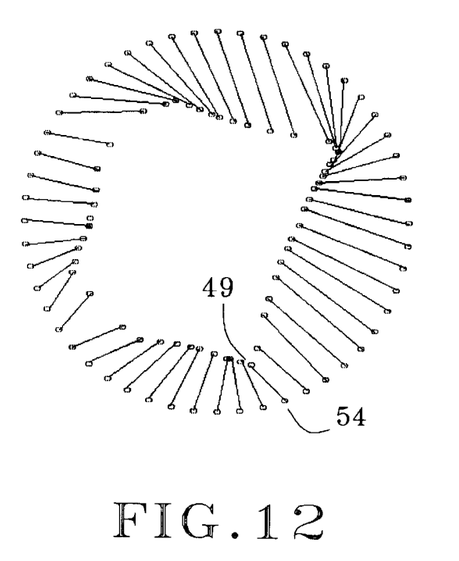
FIG. 12 suggests that the pulse group on the attractor is isomorphic to a group of fixed-step translations along a circle.

The nature of the pulse group may be further clarified by comparing it to a ,"circle group" i.e., translations along a circle by multiples of a fixed angular step. It appears that the circle group can be chosen such that the groups are isomorphic. If this is true, there must be a transformation θ=g(s) from the attractor to at least a part of a circle, θ being the angular coordinate along the circle in radians; FIG. 12 suggests such a transformation, indicated by straight lines. For instance, the pulse point 49 on the attractor transforms to the point 54 on the circle. The transformation maps the nonuniform pulse point density ρ(s) into a uniform point density ρ*(θ). The action of the circle group is to take θ to θ+α, where α is a constant. The nature of the group is determined by the fractional circle step η=α/(2π); if η is irrational, the circle group is not periodic but almost periodic. Then, the iterated images of any point on the circle come arbitrarily close to every point on the circle, so that the group is ergodic [8]. For rational η=p/q, with integers p and q relatively prime, the pulse train is periodic of order q. The integer p is called the winding number. The shape of the attractor, the pulse group, and the integers p and q are invariant under time scale transformations wherein all RC times in the device of FIGS. 5 or 6 are scaled by a common factor, while the resistors in the cross-coupling links are kept the same.

The values of the winding number p and the order q of the periodicity have meaning for the pulse group as well as for the circle group. For the group properties it does not matter how the circle is chosen, but other considerations make it convenient to choose a special circle centered at the center of gravity (λ,λ) of the q pulse points in a complete period. The radius a of the special circle is taken as the rms value of the distance between the center (λ,λ) and a pulse point, over the set of pulse points within a full period of q pulse points. The parameters λ and δ have practical significance, λ being the average pulse interval <x> over the period, and δ/λ the relative depth of the pulse variability. The average pulse interval changes with time scale transformations, but the relative depth of pulse variability does not. For excitation of a sensory resonance with resonance frequency f, the main frequency $f_m=1/\lambda$ of the pulses should be chosen close to f, "close" here meaning "within 0.2 Hz". For effective thwarting of habituation, δ/λ should be a sizable fraction of unity, the order q of periodicity should be large, and the angular circle step α should be considerable, lest the pulse interval varies so slowly that the nervous system can adapt to it. As is the case for physical measurements and numerical computations, the nervous system cannot resolve irrational numbers. Neither can it distinguish between almost periodic pulse trains and trains that are periodic of large order.

The values of the characteristic parameters for the device of FIG. 6 are determined as follows. Ideally, periodicity would be indicated by the coincidence of a pulse point and an iterated image. In practice however, the resolution limitations of the measurement instruments and the analog-to-digital converter make this test unreliable. The resolution problem can be alleviated by comparing a whole sequence of pulse points to the image of the sequence. Choosing a sequence of 15 points, the Euclidean distance was computed between 15-dimensional consecutive pulse interval vectors starting at different places in the measured train of about two hundred pulses. The calculation gave a minimum distance of 14 milliseconds which occurs for pulse interval sequences that are 88 pulses, apart. Furthermore, one finds that 88 consequitive transformation steps takes one approximately through 19 windings around the attractor. Momentarily ignoring the small violation of periodicity gives p=19 and q=88, and one therefore has in the isomorphic circle map an angular step $\alpha$ of approximately $(19/88)(2\pi)=1.3566$ radians, an order of periodicity of at least 88 and a winding number of at least 19. The average pulse interval is found to be $\lambda=1.698$ second, so that the main frequency of the pulses comes to 0.589 Hz. The relative depth of pulse variability turns out to be $\delta/\lambda=26\%$. One can increase the variability depth by decreasing the ratio of the feedback resistor $R_{78}$ or $R_{79}$ to the chip-resident 100 K$\Omega$ resistors in the voltage divider that set the normal threshold of $\frac{2}{3}$ of the supply voltage at the control voltage pins 67 and 77 shown in FIG. 5. The order q of periodicity is influenced by the ratios of the RC times of the two timers and the two feedback circuits.

Figure 13:
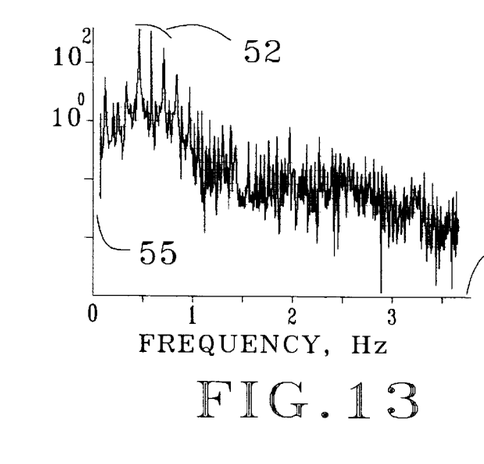
FIG. 13 shows the low-frequency part of the power spectral density for the measured output voltage of the generator of FIG. 6.
Figure 14:
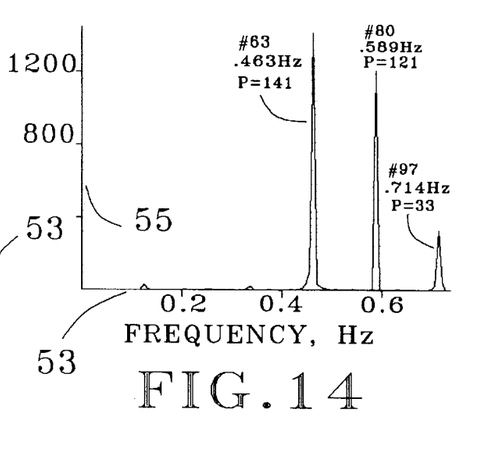
FIG. 14 shows the main peaks in the power spectrum of FIG. 13.

Additional characterization of the measured voltage signal produced by the generator of FIG. 6 may be provided through spectral analysis. FIG. 13 shows a semi-logarithmic plot of the power spectral density of the voltage signal data used for the construction of FIG. 9. In FIG. 13, the power spectral density 55 is plotted versus frequency 53. Three principal peaks 52 are noticed, and the spectrum shows no periodicity. In the linear plot of FIG. 14 the three principal peaks are shown in detail, together with their frequency bin number, frequency, and relative power P. In the spectral density plots, the frequency in Hertz is $jf_s/N$, where j=0, 1, 2, . . . , is the frequency bin number in the discrete Fourier transform, $f_s=451.1181$ Hz is the sampling frequency used in the measurements, and N=61326 is the number of voltage samples measured. The frequency resolution in the plots is about 0.007 Hertz, as follows from using $\Delta j=1$ in the above mentioned frequency expression. A signal composed of three sine waves with the frequencies of the three peaks of FIG. 14, and with amplitudes equal to the square root of the relative powers may serve as a crude simulation of the measured pulse train analyzed. The frequencies of these sine waves are $f_1=63f_s/N$, $f_2=80f_s/N$, and $f_3=97f_s/N$. The resultant pulse train formally has the period $N/f_s=135.9$ seconds, because the frequency bin numbers j=63, 80, and 97 of the sine waves are relatively prime. The formal periodicity is here equal to the duration of the measurement run, and is of course an artifact of the discrete Fourier transform. Physically, the data do not show periodicity.

Figure 15:
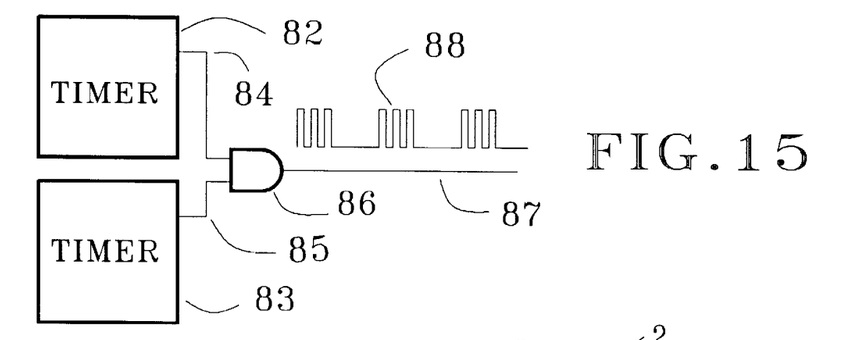
FIG. 15 shows how to obtain a composite square wave.

A complex wave may be used for the joint excitation of two different sensory resonances. A simple generator of a complex wave, suitable for the joint excitation of the ½ Hz autonomic resonance and the 2.4 Hz cortical resonance, is shown in FIG. 15. Timers 82 and 83 are arranged to produce square waves of frequencies $f_1$ and $f_2$ respectively, where $f_1$ is near 2.4 Hz, and $f_2$ is near ½ Hz. The outputs 84 and 85 of the timers are connected to the inputs of an AND gate 86. The output 87 of the AND gate is a square wave of frequency $f_1$, which is amplitude modulated by a square wave of frequency $f_2$, as indicated by the pulse train 88. The pulse train is drawn for the case with $f_1=2.4$ Hz and $f_2=0.4$ Hz.

A signal, being it voltage or electric field, is said to be periodic if it repeats after a certain time, called the period. The notions discussed above for the pulse group clearly pertain to a periodic signal as well, so that the concepts of order of periodicity, winding number, and main frequency apply. A signal is periodic of order m if its period contains m pulses. The frequency of the signal is the reciprocal of the period, and differs from the main frequency if the order m is not equal to unity. The signal 88 of FIG. 15 is periodic of order three, has a winding number equal to unity, a period of 2.5 second, a frequency of 0.4 Hz, and a main frequency of 0.83 Hz.

A signal that is periodic of order one consists of a train of identical pulses, and has a period equal to the pulse interval.

A signal composed of two sine waves is periodic if the ratio of the two frequencies is rational, and almost periodic if the ratio is irrational [10]. In practice the two cases may be indistinguishable, because of noise, and further because of limits on running time, measurement resolution, and accuracy of the data processing. Similar considerations apply when the signal is the sum of several sine waves.

Pulse variability can be arranged in other ways, such as ramping the pulse frequency in time, or switching the pulses on and off according to a certain schedule determined by dedicated digital circuitry or by a programmable microprocessor such as the basic stamp [11]. These methods of pulse variability can be implemented in well-known manner by those skilled in the art.

The excitation of the ½ Hz sensory resonance involves the autonomic nervous system. Ptosis of the eyelids is among the physiological effects of this resonance [6,7]. It has been observed that, immediately after onset of the resonance, the frequency at which ptosis is maximum slowly decreases until a steady frequency is reached in 5 to 10 minutes. This frequency is called the ptosis frequency. Autonomic responses to external pulsed electric field stimulation are observed roughly in the range of pulse frequencies from 11% below to 4% above the ptosis frequency. For pulsed electric fields with small to moderate pulse variability, autonomic effects are expected when the main frequency of the pulses falls in this range. These effects may be used to control autonomic nervous system disorders [12] such as panic attacks, stage fright, fainting spells, urinary bladder and sexual dysfunction, sleep apnea and respiratory disturbances, and certain types of pain. Calculation of the main frequency requires taking an average of pulse intervals over a set of pulses. If the pulse group is periodic, this set is taken as all pulses in a period. If the pulse group does not have a period within the "on" time of the pulse generator, then the average is simply taken over all pulses.

The afferents to be modulated by the pulsed external electric field should be chosen judiciously such as to maximize the desired effect. For instance, for the control of panic attacks and stage fright, sleep apnea and respiratory disturbances, the external electric field may be applied to skin overlying the vagus nerve in the neck, whereas control of the urinary bladder and sexual dysfunction may proceed best by applying the external electric field to skin overlying the sacral spine, or to the anus, perineum, or lower abdominal skin.

Figure 16:
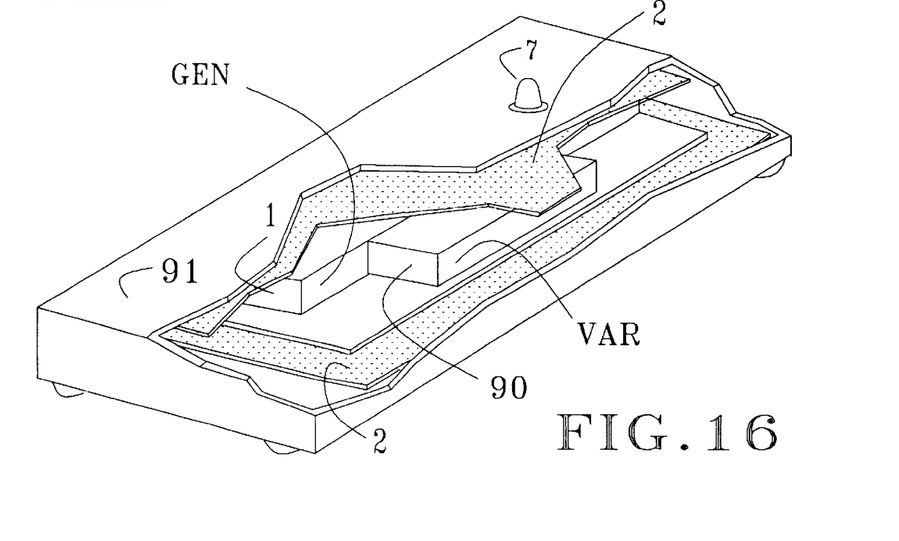
FIG. 16 shows schematically an embodiment in which the voltage pulse generator, the means for introducing pulse variability, and the field electrodes are contained in a single small casing.

The pathological oscillatory neural activity involved in epileptic seizures is influenced by the chemical milieu of the neural circuits that partake in the oscillation. Since the excitation of a sensory resonance is expected to cause a shift in neurotransmitter and hormone concentrations, external electric fields may be useful for control and perhaps treatment of seizures. For this purpose, the patient wears compact field electrodes and a voltage generator, which is to be manually activated when a seizure precursor, such as an aura, is experienced. A small box that contains the field electrodes as well as the generator, such as depicted schematically in FIG. 16, is also suitable for this purpose.

Weak electric fields suffice for the excitation of sensory resonances, if applied to a large skin area. This makes it possible to use a small and compact battery-powered device such as depicted schematically in FIG. 16, which shows the voltage pulse generator 1 labeled "GEN", the circuitry 90 labeled "VAR" for introducing pulse variability, and the field electrodes 2, all contained in a small casing 91. The pulses can be monitored with the LED 7. The area of predominant field application can be made large by placing the device at a considerable distance from the subject, typically 30 cm. At such a distance the electric field induced by the device, although weak, is spread over a large skin area, and therefore suffices for excitation of the ½ Hz sensory resonance.

The method is expected to be effective also on certain animals, and applications to animal control are therefore envisioned. The nervous system of humans is similar to that of other mammals, so that sensory resonances are expected to exist in the latter, albeit with somewhat different frequencies. Accordingly, in the present invention, subjects generally are mammals.

The invention is not limited by the embodiments shown in the drawings and described in the specification, which are given by way of example and not of limitaion, but only in accordance with the scope of the appended claims.

REFERENCES

[1] Norbert Wiener, NONLINEAR PROBLEMS IN RANDOM THEORY, p. 71–72, John Wiley & Sons, New York, 1958
[2] M. J. W. Brennan, U.S. Pat. No. 5,169,380 (1992)
[3M. Hutchison, MEGABRAIN, Ballantine Books, New York, 1991
[4] R. Stone, "Polarized Debate: EMFs and Cancer", Science 258, 1724 (1992)
[5] A. Longtin and K. Hinzer, "Encoding with Bursting, Subthreshold Oscillations, and Noise in Mammalian Cold Receptors", Neural Computation 8, 215 (1996)
[6] H. G. Loos, "Method and Apparatus for Manipulating Nervous Systems", U.S. Pat. No. 5,782,874, Jul. 21, 1998
[7] H. G. Loos, "Manipulation of Nervous Systems by Electric Fields", U.S. Pat. No. 5,899,922, May 4, 1999
[8] H. G. Schuster, DETERMINISTIC CHAOS, Physik-Verlag, Weinheim, 1984
[9] E. N. Lorentz, "Deterministic Nonperiodic Flow", J. Atmos. Sci. 20, 130 (1963)
[10] A. S. Besicovitch, ALMOST PERIODIC FUNCTIONS, Dover, 1954
[11] Basic Stamp. Parallax, Inc, http://www.parallaxinc.com
[12] AUTONOMIC FAILURE, 2nd Edition, Ed. Sir Rodger Bannister, Oxford University Press, New York, 1988

I claim:

1. Apparatus for manipulating the nervous system of a subject, comprising:

generator means for generating voltage pulses;

field electode means, connected to the generator means, for inducing electric field pulses on the skin of the subject to modulate afferent nerves without causing classical nerve stimulation; and means for introducing variability in the voltage pulses.

2. The apparatus of claim 1, further including casing means for containing the generator means, the field electrode means, and the means for introducing variability in the voltage pulses.

3. The apparatus of claim 1, wherein the voltage pulses have pulse intervals, and the generator means includes control means for influencing the pulse intervals, the control means having a control voltage port, and wherein the means for introducing variability in the voltage pulses includes a source of fluctuating voltage that is connected to the control voltage port.

4. The apparatus of claim 3, wherein the source of fluctuating voltage comprises second generator means for generating voltage pulses, the last said voltage pulses having pulse intervals, the second generator means including second control means for influencing the last said pulse intervals, the second control means having a second control voltage port, and the first said generator means is connected to the second control voltage port.

5. A method for manipulating the nervous system of a subject, comprising the step, of:

selecting on the subject a skin area;

generating voltage pulses;

applying the voltage pulses to field electrodes for inducing electric field pulses on said skin area to modulate afferent nerves without causing classical nerve stimulation; and introducing variability in the voltage pulses.

6. The method of claim 5 wherein the step of introducing variability in the voltage pulsed includes:

generating second voltage pulses;

arranging the second voltage pulses to influence first said voltage pulses; and arranging the first said voltage pulses to influence the second voltage pulses.

7. The method of claim 5 for exciting in the subject a sensory resonance which has a resonance frequency, the voltage pulses having a main frequency, the method further including the step of setting the main frequency close to the resonance frequency.

8. The method of claim 5 for controlling in the subject a pathological oscillatory activity of neural circuits, such as tremors and seizures, the voltage pulses having a main frequency, the method further including the step of adapting the main frequency and the variability in the voltage pulses to control the pathological oscillatory activity.

9. The method of claim 8 where the pathological oscillatory activity involves seizures, further including the step of switching on the voltage generator when a precursor to the seizures is detected.

10. The method of claim 5 for controlling in the subject autonomic nervous system disorders, the subject having a ptosis frequency, the voltage pulses having a main frequency, the method further including the step of setting the main frequency in the range from 11% below to 4% above the ptosis frequency.

11. The method of claim 5 for inducing in the subject sexual excitement, wherein said skin area includes at least part of the skin covering the scrotum, perineum, anus, and sacral spine.

* * * * *